US 8,263,786 B2
Sep. 11, 2012

(12) United States Patent
Yasumura et al.

(54) METHODS FOR PRODUCING CYCLIC PHENOL SULFIDES

(75) Inventors: Masateru Yasumura, Tsukuba (JP); Yoshikazu Aoki, Koriyama (JP); Masami Ito, Tsukuba (JP); Masafumi Umekawa, Motomiya (JP); Naohiro Tarumoto, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 536 days.

This patent is subject to a terminal disclaimer.

(21) Appl. No.: 12/439,121

(22) PCT Filed: Aug. 29, 2007

(86) PCT No.: PCT/JP2007/066758
§ 371 (c)(1),
(2), (4) Date: Apr. 9, 2009

(87) PCT Pub. No.: WO2008/026636
PCT Pub. Date: Mar. 6, 2008

(65) Prior Publication Data
US 2009/0264661 A1    Oct. 22, 2009

(30) Foreign Application Priority Data
Aug. 29, 2006 (JP) .................. 2006-231535

(51) Int. Cl.
*C07D 341/00* (2006.01)
(52) U.S. Cl. ........................................ 549/11
(58) Field of Classification Search ............ 549/11
See application file for complete search history.

(56) References Cited

U.S. PATENT DOCUMENTS
5,824,808 A    10/1998 Hori et al.
7,901,858 B2 *  3/2011 Yasumura et al. ........ 430/108.5

FOREIGN PATENT DOCUMENTS
| EP | 0 731 102 A1 | 11/1996 |
| JP | 09-227553 | 9/1997 |
| JP | 10-081680 | 3/1998 |
| JP | 11-049770 | 2/1999 |
| JP | 2000-273096 | 10/2000 |
| JP | 2002-193963 | 7/2002 |
| JP | 2002-255961 | 9/2002 |

OTHER PUBLICATIONS

Kumagai, English Machine Translation of Production of Cyclic Phenol Sulfide, JP Pub No. 11-049770, Feb. 1999, p. 1-5.*
Kumagai, H., et al., "Facile Synthesis of p-tert-Butylthiacalix[4]arene by the Reaction of p-tert-Butylphenol with Elemental Sulfur in the Presence of a Base", Tetrahedron Letters, vol. 38, No. 22, 3971-3972, (1997).
Extended European Search Report for EP 07806235.3, dated Aug. 5, 2010.
Iki et al.; Synthesis of p-tert-Butylthiacalix[4]arene and its Inclusion Property; Tetrahedron vol. 56, No. 11 (2000); pp. 1437-1443.

* cited by examiner

*Primary Examiner* — Golam M M Shameem
*Assistant Examiner* — Karen Cheng
(74) *Attorney, Agent, or Firm* — Hoffman & Baron, LLP

(57) ABSTRACT

The object of the present invention is, in methods for producing cyclic phenol sulfides, to provide methods for producing a number of more macrocyclic products, which comprise the steps of producing a mixture of cyclic phenol sulfides from an inexpensive raw material in one step without inducing the reduction in yield of a cyclic quatromer; and easily separating and purifying a single component from the mixture of cyclic phenol sulfides.

The present invention discloses methods for producing a cyclic phenol sulfide which comprises the step of reacting a phenol compound as a raw material, in a one-step reaction, with 1.7 to 2.5 molar equivalent of sulfur and 0.25 to 0.75 molar equivalent of an alkali metal reagent per 1 mol of the phenol compound to obtain a mixture of cyclic phenol sulfide wherein m=4 and at least one kind(s) of cyclic phenol sulfide wherein m=5 to 9, or each separate cyclic phenol sulfide comprised in the mixture.

6 Claims, No Drawings

METHODS FOR PRODUCING CYCLIC PHENOL SULFIDES

CROSS-REFERENCE TO RELATED APPLICATIONS

This application is a National Stage of International Application No. PCT/JP2007/066758, filed Aug. 29, 2007, which claims the benefit of Japanese Application No. 2006-231535, filed Aug. 29, 2006, the contents of all of which are incorporated by reference herein in their entirety.

FIELD OF THE INVENTION

The present invention relates to methods for producing cyclic phenol sulfides, which are useful as metal capture agents or solidifying agents wherein the metal-ion capturing ability thereof is used; optical sensors, ion sensors or substrate specific sensors wherein the recognizing ability of ions or molecules is used; materials for separation membranes and intermediates thereof; charge control agents; catalysts, and the like.

BACKGROUND OF THE INVENTION

Methods for producing cyclic phenol sulfides include the method which comprises the steps of using a phenol compound, sulfur and an alkali metal reagent as raw materials and synthesizing them by heating (for example, see Patent Literatures 1-2, and Non-patent Literature 1). These methods are easy and practical production methods wherein the objects can be obtained in one operation and an inexpensive raw material is used. However, the distribution of the products tends to be focused in a cyclic quatromer wherein m=4 in the formula (2). Besides it, when obtaining more macrocyclic products wherein m=5 to 9 in the formula (2), the collection of a cyclic quartromer is not taken account, and the overall yield is not considered. In the purification process, column chromatography is required. Further, there is the method which comprises the steps of using a chain phenol sulfide, sulfur and an alkali metal reagent as raw materials and synthesizing them by heating (for example, see Patent Literatures 3 to 6). Though these methods make it possible to produce a number of more macrocyclic products wherein m=5 to 9 in the formula (2), the yield of a cyclic quatromer becomes less. In addition, the methods comprise two steps, that is, the step of producing a chain phenol sulfide from a phenol compound, and the step of cyclizing the chain phenol sulfide to produce a cyclic phenol sulfide. Thus, they are industrially unfit.

Patent Literature 1: JP-A9-227553
Patent Literature 2: JP-A2002-193963
Patent Literature 3: JP-A 10-081680
Patent Literature 4: JP-A 11-049770
Patent Literature 5: JP-A 2000-273096
Patent Literature 6: JP-A 2002-255961
Non-patent Literature 1: H. Kumagai et al., Tetrahedron Lett.(1997), 38, 3971-3972

SUMMARY OF THE INVENTION

The object of the present invention is, in methods for producing cyclic phenol sulfides, to provide methods for producing a number of more macrocyclic products, which comprise the steps of producing a mixture of cyclic phenol sulfides from an inexpensive raw material in one step without inducing the reduction in yield of a cyclic quatromer; and easily separating and purifying a single component from the mixture of cyclic phenol sulfides.

The inventors thoroughly searched to solve the above problems and found a method comprising the step of using a phenol compound of the following formula (1) as a raw material:

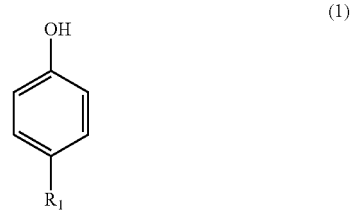

wherein R1 represents a straight or branched alkyl group having 1 to 6 carbon atoms,
in a one-step reaction, and thereby easily producing a cyclic phenol sulfide of the following formula (2) in high yields:

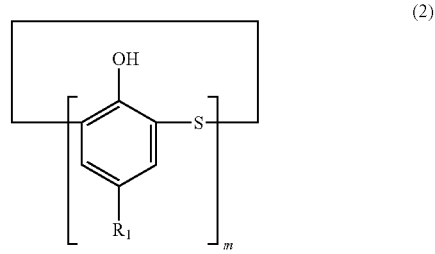

wherein R1 represents a straight or branched alkyl group having 1 to 6 carbon atoms, and m is an integer from 4 to 9. They also found a method comprising the step of separating and purifying a single component from the mixture of cyclic phenol sulfides of the formula (2) obtained by the reaction without conducting the complicated purification. The present invention has been completed based on these findings.

Namely, the present invention provides a method for producing a cyclic phenol sulfide of the above formula (2) which comprises the step of heating and reacting a phenol compound of the above formula (1), a specific amount of sulfur and a specific amount of an alkali metal reagent as raw materials in a solvent.

The present invention also provide a method which comprises the steps of using a lower alcohol as a solvent for crystallization and separating a cyclic quatromer from a mixture of the cyclic phenol sulfides obtained by the above production method; then using various organic solvents as a solvent for crystallization to separate more macrocyclic cyclic phenol sulfides wherein m=5 to 9 in the formula (2) into each component.

According to the method for producing a cyclic phenol sulfide of the present invention, the yield of a cyclic quatromer is not decreased though increasing the yield of more macrocyclic cyclic phenol sulfides wherein m=5 to 9 in the formula (2). In addition, the method makes it possible to easily produce a cyclic phenol sulfide of the formula (2) in high yields with maintaining the easiness that two or more kinds of products are produced in one step.

Further, the method for producing a cyclic phenol sulfide of the present invention makes it possible to separate and purify a single component wherein m=4 to 9 in the formula (2) into each component from a cyclic phenol sulfide of the formula (2), by an easy crystallizing operation with various organic solvents as a solvent for crystallization and without conducting a complicated recrystallization wherein several solvents are combined; or column chromatography which increases the production cost since it requires a massive amount of a solvent(s).

DETAILED DESCRIPTION OF THE INVENTION

In a phenol compound of the formula (1) which is a raw material of the present invention, examples of a straight or branched alkyl group having 1 to 6 carbon atoms (R1) include following groups: a methyl group, ethyl group, n-propyl group, 2-propyl group, n-butyl group, sec-butyl group, 2-methylpropyl group, tert-butyl group, n-pentyl group, 1-methylbutyl group, 1-ethylpropyl group, 1,1-dimethylpropyl group, 1,2-dimethylpropyl group, n-hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbutyl group, 1,3-dimethylbutyl group, 1,4-dimethylbutyl group, 2,2-dimethylbutyl group, 2,3-dimethylbutyl group, 3,3-dimethylbutyl group, 1-ethyl-2-methyl-propyl group, and 1,1,2-trimethylpropyl group.

Next, the method for producing a cyclic phenol sulfide of the present invention is illustrated. In the method for producing a cyclic phenol sulfide of the present invention, it is preferable that the cyclizing reaction is conducted in the presence of a solvent(s). The preferable usage amount of the solvent(s) is 0.1 to 1 L and more preferably 0.3 to 0.6 L per 1 mol of a phenol compound of the formula (1) which is a raw material. The kind of the solvents includes saturated aliphatic ethers, aromatic ethers, saturated aliphatic thioethers, aromatic thioethers, saturated aliphatic hydrocarbons, and aromatic hydrocarbons. Aromatic ethers, aromatic thioethers and aromatic hydrocarbons are preferable among them, and diphenyl ether is particularly preferable.

In the present invention, the feed molar ratio of sulfur to a phenol compound of the formula (1) is preferably 1.7 to 2.5 molar equivalent of sulfur to 1 mol of the phenol compound, and particularly preferably 1.9 to 2.1 molar equivalent thereof.

In the present invention, various alkali metal reagents such as alkali metals, hydrogenated alkali metals, carbonic alkali metals and alkali metal alkoxides are usable, and alkali metal hydroxides are preferable. Examples of alkali metal hydroxides include lithium hydroxide, sodium hydroxide, and potassium hydroxide. Sodium hydroxide is particularly preferable.

The preferable usage amount of an alkali metal reagent is 0.25 to 0.75 molar equivalent and particularly preferably 0.4 to 0.6 molar equivalent per 1 mol of a phenol compound of the formula (1).

In the present invention, it is preferable that the cyclizing reaction is conducted under an inactive gas atmosphere, and it is further preferable that the reaction is conducted while introducing an inactive gas into the reaction system. Examples of the inactive gas include nitrogen, helium and argon, and the kind thereof is not particularly limited in practicing the present invention.

In the present invention, the production is conducted while removing water and hydrogen sulfide each of which is generated in the cyclizing reaction. The generated water and hydrogen sulfide are removed from the system by introducing an inactive gas into the system or by the suction under slightly reduced pressure without boiling a solvent(s). Then, they are continuously captured by being absorbed into an alkaline aqueous solution such as an aqueous solution of sodium hydroxide or an amine solution such as ethanolamine; or by being adsorbed on activated carbon, molecular sieve, iron oxide, zinc oxide, or the like.

In the present invention, it is preferable that the reaction temperature of the cyclizing reaction is risen in three steps. Though the intended compound can be obtained by rising the temperature to the final reaction temperature in one step, it induces the decrease in the yield thereof. Thus, it is preferable to rise the temperature in three steps. Namely, the reaction temperature is heated up to 120 to 140° C. (the first step) and kept in the same temperature for 0.5 hour or more. Though there is no upper limit of the reaction time thereof, 0.5 to 8 hours is preferable since more than that increases the production cost. Subsequently, the reaction temperature is heated up to 160 to 180° C. (the second step) and kept in the same temperature for 0.5 hour or more. Though there is no upper limit of the reaction time thereof, 0.5 to 8 hours is preferable since more than that increases the production cost. Finally, the reaction temperature is heated up to 210° C. or higher (the third step). Even if the reaction temperature herein is 200° C. or higher, a cyclic quatromer produces. However, in order to produce a number of more macrocyclic cyclic phenol sulfides wherein m=5 to 9 in the formula (2), it is preferable to rise the reaction temperature to 210° C. or higher. Though there is no upper limit of the reaction temperature, 240° C. or lower is preferable since more than that increases the production cost. Though the reaction time changes depending on the reaction temperature and the kind of a phenol compound which is a raw material, it is preferable to set the time to 1 to 30 hours.

The reaction product of the present invention can be obtained by adding an aqueous solution of a mineral acid to the reaction mixture of the cyclizing reaction. Examples of the used mineral acid include a sulfuric acid, a hydrochloric acid, a nitric acid, a phosphoric acid, a boric acid and the like, and the kind thereof is not particularly limited in practicing the present invention. The preferable amount of the mineral acid is 0.5 to 3.0 molar equivalent per 1 mol of a phenol compound of the formula (1).

Though the above reaction product can be separated and purified by the ordinary separation method such as column chromatography, recrystallization, or the combination thereof, the following method makes it possible to more effectively and easily separate and purify a cyclic quatromer and more macrocyclic cyclic phenol sulfides wherein m=5 to 9 in the formula (2).

Namely, the method comprises the steps of using a lower alcohol as a solvent for crystallization and separating a cyclic quatromer; and then using various organic solvents as a solvent for crystallization to separate and purify more macrocyclic cyclic phenol sulfides wherein m=5 to 9 in the formula (2) into each component. The lower alcohol used in the present invention is a straight or branched alcohol having 1 to 4 carbon atoms. Examples thereof include methanol, ethanol, propanol, 2-propanol, and butanol. Methanol, ethanol and 2-propanol are preferable among them, and methanol is particularly preferable. As for the feed amount of the lower alcohol used as a solvent for crystallization, it is preferable to use 0.2 to 5 by weight and particularly preferably 0.5 to 1.5 by weight thereof per the amount of the solvent used in the reaction. It is particularly preferable to use 100 to 300 parts by weight of a lower alcohol per 100 parts by weight of the reaction mixture. Further, the crystallization temperature is preferably 20 to 80° C. and particularly preferably 40 to 60° C.

In the present invention, a cyclic quatromer may be precipitated by adding an aqueous solution of a mineral acid to the reaction product after the completion of the cyclizing reaction, and then adding a lower alcohol thereto. Or it may also be precipitated by adding a lower alcohol to the reaction product, and then adding an aqueous solution of a mineral acid thereto.

In the present invention, the temperature at which a precipitated cyclic quatromer by a lower alcohol is separated may be any proper temperature, and 30° C. or higher is preferable, and 40 to 60° C. is more preferable. The separation of a cyclic quatromer can be conducted by the ordinary separation method such as filtration under reduced pressure, pressure filtration, centrifugation, filter press, and the like. Further, it is allowable to conduct a washing operation with the lower alcohol or water in order to produce more highly pure separated cyclic quatromer.

In the present invention, when cooling a separation solution which separated a cyclic quatromer, an organic solvent layer solidifies. Though the cooling temperature varies depending on a used phenol compound of the formula (1) or the kind of used lower alcohols, 0 to 25° C. is preferable. The temperature at which the solidified substance is separated after the solidification of the separation solution may be any proper temperature. However, in order to maximally exercise the effect of the present invention, the separation is conducted preferably at lower than 30° C., and more preferably −10 to 20° C. The separation of the solidified substance can be conducted by the ordinary separation method such as filtration under reduced pressure, pressure filtration, centrifugation, filter press, and the like.

In the present invention, it is possible to separate and purify more macrocyclic cyclic phenol sulfides wherein m=5 to 9 in the formula (2) into each component by adding various organic solvents as a solvent for crystallization to the separated solidified substance. The kind of a solvent for crystallization, the feed amount, crystallization temperature and the like are variously selected according to the kind of an intended cyclic phenol sulfide.

Further, it is allowable to conduct a washing operation with the lower alcohol or water in order to produce more highly pure separated cyclic phenol sulfide.

In the present invention, examples of organic solvents added to the separated solidified substance as a solvent for crystallization include methanol, ethanol, acetone, methyl ethyl ketone, hexane, heptane, octane, cyclohexane, toluene, xylene, ethyl acetate, butyl acetate, diethyl ether, diisopropyl ether, and cyclopentyl methyl ether. The solvent is not particularly limited only if it is the solvent in which an intended cyclic phenol sulfide is less soluble.

Next, Examples will further illustrate the present invention. They only explain the present invention and do not particularly limit the invention. The purity and relative proportions of a cyclic phenol sulfide of the present invention were analyzed by a high-performance liquid chromatography (herein after referred to as HPLC). The measurement condition of HPLC is as follows: device: LC-6A by Shimadzu Corporation; column: Develosil ODS-HG-5 (inside diameter 4.6, column length 250 mm) by Nomura Chemical Co., Ltd.; column temperature: 40° C.; mobile phase: tetrahydrofuran/acetonitrile/water/trifluoroacetic acid=450/400/150/2 (v/v/v/v); current speed: 1.0 mL/min.; filling amount: 1 μL; and concentration of a sample: 1000 ppm.

EXAMPLES

Example 1

45.1 g of 4-tert-butylphenol, 19.2 g of sulfur (twofold mol per 1 mol of 4-tert-butylphenol) and 6.0 g of sodium hydroxide (a half mol per 1 mol of 4-tert-butylphenol) were poured in a 500 mL four-neck flask with a mixer, a cooling tube, a thermometer and a gas-introducing tube. 102 g of diphenyl ether was added thereto and heated up to 130° C. with stirring the mixture in the current of nitrogen gas. The reaction was conducted for 1 hour at 130° C. Then, the temperature was risen to 170° C., and the reaction was conducted for 1 hour at 170° C. Finally, after heating the mixture up to 230° C., the reaction was conducted for 12 hours at 230° C. The above reactions were conducted removing generated water and hydrogen sulfide by the method comprising the steps of letting nitrogen into the reactor and pushing water and hydrogen sulfide out to the system; and contacting them to an aqueous solution of sodium hydroxide to absorb them. The reaction mixture was cooled down to room temperature and neutralized by adding 40 mL of an aqueous solution of 3 mol/L sulfuric acid thereto. Then, 25 mL of toluene and 70 mL of n-hexane were added thereto to precipitate crystals. The crude crystals were filtered and washed twice with 80 mL of acetone and 80 mL of water, and then 80 mL of acetone. As a result of analyzing the obtained crude crystals (yield 41.9 g) with HPLC, it was clarified that the crystals were a mixture which comprises a cyclic quatromer wherein R1 is tert-butyl and m=4 in the formula (2) indicating the peak area ratio of 93.8%; and a cyclic octamer wherein R1 is tert-butyl and m=8 in the formula (2) indicating the peak area ratio of 5.2%.

Example 2

The same cyclizing reaction and the neutralization with an aqueous solution of a sulfuric acid were conducted under the same condition as that of Example 1. 79.1 g of methanol was added to the obtained reaction mixture after the neutralization and heated up to 55° C. Then, the mixture was stirred for 1 hour to precipitate crude crystals of a cyclic quatromer wherein R1 is tert-butyl and m=4 in the formula (2). The crude crystals were filtered under reduced pressure, and the obtained crude crystals were washed with 80 g of methanol and further with 80 g of water. The obtained cyclic quatromer was 40.2 g, and the yield on the 4-tert-butylphenol basis was 74.4%, which was a high yield. As a result of HPLC analysis, the purity indicated the peak area ratio of 98.2%.

The structure of the obtained cyclic quatromer was identified by IR. IR (Nujol) cm$^{-1}$: 3243, 1475, 1407, 1393, 1267, 1246, 886, 823, 740.

Subsequently, the filtrate after filtering the above cyclic quatromer under reduced pressure was cooled down to 5° C. with stirring to solidify it. The solidified substance was filtered at 5° C., and thus obtained solidified substance was washed twice with 100 mL of 10° C. water. 60 g of n-hexane was added to the substance and a left insoluble substance was filtered out, said substance which is a cyclic octamer wherein R1 is tert-butyl and m=8 in the formula (2). Thus obtained cyclic octamer was 1.3 g, and the yield on the 4-tert-butylphenol basis was 2.4%, which was a high yield. As a result of HPLC analysis, the purity indicated the peak area ratio of 93.9%.

The structure of the obtained cyclic octamer was identified by IR. IR (Nujol) cm$^{-1}$: 3328, 1475, 1391, 1277, 1244, 887, 819, 750.

Example 3

A cyclic phenol sulfide was produced by the same method as that of Example 1, except that 2.5-fold mol of sulfur was used per 1 mol of 4-tert-butylphenol. As a result, a mixture was obtained, said mixture which comprises a cyclic quatromer indicating the peak area ratio of 95.1%; and a cyclic octamer indicating the peak area ratio of 4.1%.

Example 4

A cyclic phenol sulfide was produced by the same method as that of Example 1, except that 0.25-fold mol of sodium hydroxide was used per 1 mol of 4-tert-butylphenol. As a result, a mixture was obtained, said mixture which comprises a cyclic quatromer indicating the peak area ratio of 96.1%; and a cyclic octamer indicating the peak area ratio of 3.0%.

Example 5

A cyclic phenol sulfide was produced by the same method as that of Example 1, except that 0.75-fold mol of sodium hydroxide was used per 1 mol of 4-tert-butylphenol. As a result, a mixture was obtained, said mixture which comprises a cyclic quatromer indicating the peak area ratio of 94.4%; and a cyclic octamer indicating the peak area ratio of 2.7%.

Comparative Example 1

A cyclic phenol sulfide was produced by the same method as that of Example 1, except that sodium hydroxide was used in the molar ratio of 1.0:1 per phenol. As a result of analyzing a product with HPLC, a cyclic quatromer wherein R1 is tert-butyl and m=4 in the formula (2) indicated the peak area ratio of 93.1% to the entire peak area, and a cyclic octamer wherein R1 is tert-butyl and m=8 in the formula (2) indicated trace amounts.

Comparative Example 2

A cyclic phenol sulfide was produced by the same method as that of Example 1, except that the final reaction temperature in the cyclizing reaction was changed to 200° C. As a result of analyzing a product with HPLC, a cyclic quatromer wherein R1 is tert-butyl and m=4 in the formula (2) indicated the peak area ratio of 97.7%, and a cyclic octamer wherein R1 is tert-butyl and m=8 in the formula (2) indicated trace amounts.

Comparative Example 3

A cyclic phenol sulfide was produced by the same method as that of Example 2, except that n-hexane was used instead of methanol in Example 2. Though a filtrate after filtering the cyclic quatromer wherein R1 is tert-butyl and m=4 in the formula (2) was cooled down to 5° C., it was not solidified. Thus, it was impossible to take out a cyclic octamer wherein R1 is tert-butyl and m=8 in the formula (2).

Comparative Example 4

The same cyclizing reaction and the neutralization with an aqueous solution of a sulfuric acid were conducted as those of Example 1. A cyclic octamer wherein R1 is tert-butyl and m=8 in the formula (2) was taken out from the obtained reaction mixture after the neutralization by column chromatography (carrier: 1.1 kg of silica gel). The obtained cyclic octamer was 0.72 g, and the yield on the 4-tert-butylphenol basis was 2.6%, which was a low yield. In addition, 15.5 L of a developing solvent (toluene/chloroform), which is a massive amount, was required in the purification process by column chromatography.

Comparative Example 5

A cyclic phenol sulfide was produced by the same method as that of Example 1, except that 1.5-fold mol of sulfur was used per 1 mol of 4-tert-butylphenol. As a result, a mixture was obtained, said mixture which comprises a cyclic quatromer indicating the peak area ratio of 96.9%; and a cyclic octamer indicating the peak area ratio of 1.6%.

According to the method of the present invention, it becomes possible to easily produce a cyclic phenol sulfide of the formula (2) in high yields by a one-step reaction using a phenol compound of the formula (1) as a raw material. Further, it also becomes possible to easily separate and purify a single component from a mixture of the cyclic phenol sulfides of the formula (2) obtained by the reaction without conducting the complicated purification.

What is claimed is:

1. A method for producing a cyclic phenol sulfide which comprises the step of reacting a phenol compound of the following formula (1) as a raw material:

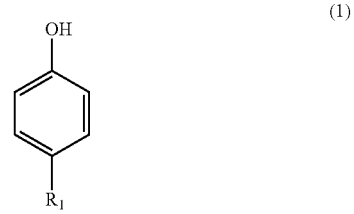

wherein R1 represents a straight or branched alkyl group having 1 to 6 carbon atoms, in a one-step reaction, with 1.7 to 2.5 molar equivalent of sulfur and 0.25 to 0.75 molar equivalent of an alkali metal reagent per 1 mol of the phenol compound to obtain a mixture of cyclic phenol sulfide wherein m=4 and at least one kind(s) of cyclic phenol sulfides wherein m=5 to 9, or each separate cyclic phenol sulfide comprised in the mixture, the cyclic phenol sulfide being represented by the following formula (2):

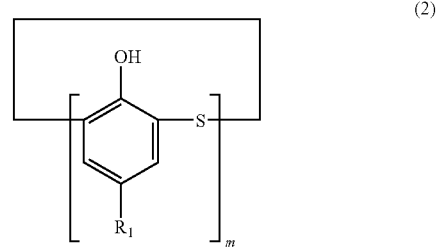

wherein R1 represents a straight or branched alkyl group having 1 to 6 carbon atoms, and m is an integer from 4 to 9; and wherein the reaction is conducted under the temperature conditions that the reaction temperature is risen to 120 to 140° C. and kept at the same temperature for 0.5 hour or more; then, it is risen to 160 to 180° C. and kept at the same temperature for 0.5 hour or more; and then it is risen to 210° C. or higher.

2. The method according to claim 1, wherein the alkali metal reagent is sodium hydroxide.

3. The method according to claim 1, which comprises the steps of using a lower alcohol as a solvent for crystallization and separating a cyclic quatromer wherein m=4 in the formula (2) from a mixture obtained by reacting the phenol compound of the formula (1) with sulfur and the alkali metal reagent; then using an organic solvent as a solvent for crystallization to separate more macrocyclic cyclic phenol sulfides wherein m=5 to 9 in the formula (2) into each component.

4. The method according to claim 3, wherein 100 to 300 parts by weight of the lower alcohol is used per 100 parts by weight of the reaction mixture.

5. The method according to claim 3, wherein the lower alcohol is methanol.

6. The method according to claim 3, wherein the crystallization is conducted at 20 to 80° C.

* * * * *